United States Patent
Scheib (10) Patent No.: US 7,720,531 B2
(45) Date of Patent: May 18, 2010

(54) METHOD AND SYSTEM FOR ANALYZING AND PRESENTING AN ELECTROENCEPHALOGRAM (EEG)

(76) Inventor: Christopher Scheib, 110 Country Knoll, Nicholasville, KY (US) 40356

( * ) Notice: Subject to any disclaimer, the term of this patent is extended or adjusted under 35 U.S.C. 154(b) by 185 days.

(21) Appl. No.: 12/082,842

(22) Filed: Apr. 15, 2008

(65) Prior Publication Data

US 2009/0259136 A1    Oct. 15, 2009

(51) Int. Cl.
*A61B 5/04*    (2006.01)
(52) U.S. Cl. .......................... 600/544; 600/545
(58) Field of Classification Search .............. 600/300, 600/544, 545, 26; 340/575–576
See application file for complete search history.

(56) References Cited

U.S. PATENT DOCUMENTS 5,813,993 A * 9/1998 Kaplan et al. ............... 600/544

* cited by examiner

*Primary Examiner*—Robert L Nasser
*Assistant Examiner*—Michael D'Angelo
(74) *Attorney, Agent, or Firm*—Stockwell & Smedley, PSC (57) ABSTRACT

A system and method determines from EEG signals the lack of awareness and the depth of anesthesia of a patient to whom an anesthetic agent is being administered. In particular, a log-log representation of the EEG power spectrum is converted to two intersecting lines so that the intersection point and the relative slopes can be analyzed to determine a state of awareness of a patient. This system and method may also be used in an analysis of the brain function of a sleeping individual to distinguish between different levels of non-REM sleep, REM sleep, and awakeness.

21 Claims, 12 Drawing Sheets

Alpha

Beta

Theta

Delta  ] 50μV

METHOD AND SYSTEM FOR ANALYZING AND PRESENTING AN ELECTROENCEPHALOGRAM (EEG)

BACKGROUND OF THE INVENTION

1. Field of the Invention

The present invention relates generally to monitoring brain function during different states of consciousness such as general anesthesia or natural sleep and, more particularly, to using electroencephalogram (EEG) data to monitor brain function.

2. Description of Related Art

The definition of the term "anesthesia" is—a lack of aesthesia—or lack of sensation. For surgical purposes this is generally achieved in two main ways: 1) infiltration of a peripheral or more central nerve bundle with a local anesthesia, which prevents the nerve impulse being processed by the central nervous system and, thus, sensation (of pain or otherwise is not perceived by the individual who remains conscious and aware; and 2) general anesthesia which requires a loss of consciousness in order for the sensation not to be perceived by the individual. To date no systems of monitoring brain function has produced a reference point beyond which one can absolutely state that there exists a complete lack of consciousness at an anesthetic dosage level low enough to be of practical value. Present systems merely produce a measure of probability of loss of consciousness when the anesthetic dosage level is at the low end of the practical range.

The "depth of anesthesia" generally describes the extent to which consciousness is lost following administration of an anesthetic agent. As the magnitude of anesthetization, or depth of anesthesia, increases, an anesthetized patient typically fails to successively respond to spoken commands, loses the eyelid reflex, loses other reflexes, undergoes depression of vital signs, and the like. Once consciousness is lost there is a progression of effects on brain function as higher concentrations or dose of anesthetic agent are administered.

While loss of consciousness and the loss of awareness of sensation are significant features of anesthesia, it should be noted that balanced high quality anesthesia must also consider muscle relaxation, suppression of the autonomous nervous system, and blockade of the neuro muscular junction. Sufficient muscle relaxation is required to ensure optimal operating conditions for the surgeon manipulating the patient's tissue. The autonomic nervous system, if not suppressed, causes the patient to respond to surgical activity with a shock reaction that effects heavily on hemodynamics and the endocrine system. To keep the patient completely motionless, the neuro muscular junctions transmitting orders from the brain to the muscles of the body need to be blocked so that the body of the patient becomes completely paralyzed.

While the need to determine the state of all five components of anesthesia is widely recognized, ascertaining loss of awareness in a reliable, accurate, and quick manner has been, and is, the subject of extensive attention. One reason for this is its importance. If the anesthesia is not sufficiently deep, the patient may maintain or gain consciousness during a surgery, or other medical procedure, resulting in an extremely traumatic experience for the patient which may have long term consequences such as post traumatic stress disorder. On the other hand, excessively deep anesthesia reflects an unnecessary consumption of anesthetic agents, most of which are expensive. Anesthesia that is too deep requires increased medical supervision during the surgery recovery process and prolongs the period required for the patient to become completely free of the effects of the anesthetic agent. A second reason for the continuing study and attention being given this field is because of its difficulty. Multiple agents are given to the patient. These agents paralyze or inhibit cardiovascular responses without producing unconsciousness. Therefore, it is possible to have a patient aware during surgery and not move or have a change in heart rate or blood pressure. A method to monitor brain function that can reliably detect consciousness or the lack of consciousness would be useful.

It has long been known that the neurological activity of the brain is reflected in biopotentials available on the surface of the brain and on the scalp. Thus, efforts to quantify the extent of anesthesia have turned to a study of these biopotentials. The biopotential electrical signals are usually obtained by a pair, or plurality of pairs, of electrodes placed on the patient's scalp at locations designated by a recognized protocol and a set, or a plurality of sets or channels, of electrical signals are obtained from the electrodes. These signals are amplified and filtered. The recorded signals comprise an electroencephalogram or EEG.

Figure 1A:
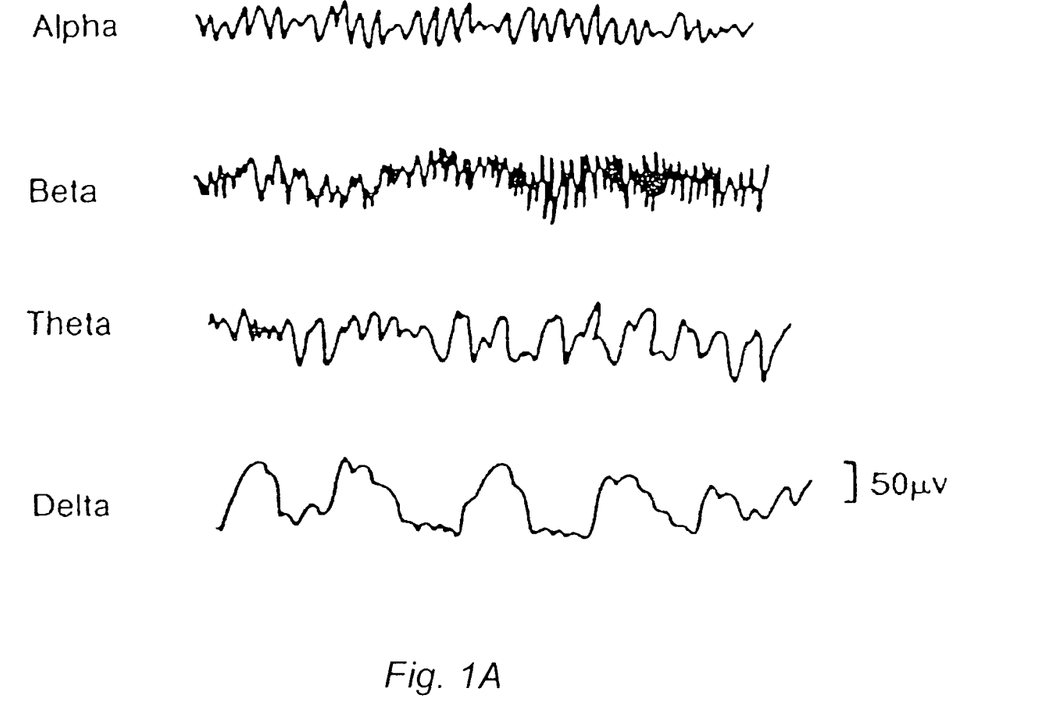
FIG. 1A shows a conventional representation of the four bands of an EEG signal.

A typical EEG is shown in FIG. 1. A macro characteristic of EEG signal patterns is the existence of broadly defined low frequency rhythms or waves occurring in certain frequency bands. Four such bands are recognized: Delta (0.5-3.5 Hz), Theta (3.5-7.0 Hz), Alpha (7.0-13.0 Hz) and Beta (13.0-32.0 Hz). Alpha waves are found during periods of wakefulness and may disappear entirely during sleep. The higher frequency Beta waves are recorded during periods of intense activation of the central nervous system. The lower frequency Theta and Delta waves reflect drowsiness and periods of deep sleep.

By analogy to the depth of sleep, it can be said that the frequency of the EEG will decrease as the depth of anesthesia increases, while the magnitude of the signal usually increases. However, this gross characterization is too imprecise and unreliable to use as an indication of such a critical medical aspect as the extent of anesthesia. Further, EEG signal changes during anesthesia may not fully correlate with changes in the hypnotic state of the patient.

The foregoing circumstance has led to the investigation and use of other techniques to study EEG waveforms to ascertain the underlying condition of the brain, including the depth of anesthesia to which a patient is subjected. It will be immediately appreciated from FIG. 1A that EEG signals are highly random in nature. Unlike other biopotential signals, such as those of an electrocardiogram (ECG), an EEG normally has no obvious repetitive patterns, the morphology and timing of which can be conveniently compared and analyzed. Nor does the shape of the EEG waveform correlate well to specific underlying events in the brain. Hence, except for certain phenomena, such as epileptic seizures, which are readily apparent from visual inspection of an EEG, the indication of other conditions in the brain in the EEG is much more subtle.

Prefatory to the use of other techniques, the EEG signals are subjected to analog to digital signal conversion by sequentially sampling the magnitude of the analog EEG signals and converting same to a series of digital data values. The sampling is typically carried out at a rate of 100 Hz or greater. The digital signals are stored in the magnetic or other storage medium of a computer and then subjected to further processing to ascertain the underlying state of the brain.

Some of the techniques by which EEG signals can be analyzed in an effort to determine the depth of anesthesia are well described in Ira J. Rampil, A Primer for EEG Signal Processing in Anesthesia, Vol. 89, Anesthesiology No. 4, pgs. 980 et seq., October 1998. Both frequency-domain analysis and time-domain analysis techniques have been considered.

Frequency-domain analysis analyzes the spectrum of frequency signals obtained from the transform to determine characteristics and features occurring in wave forms having the various frequencies of the spectrum. The results of an EEG frequency-domain analysis are typically graphically displayed as a power versus frequency histogram in which frequency is graphed on the abscissa and power is graphed on the ordinate.

Further efforts to obtain useful information from electroencephalograms have employed higher order analyses, including the bispectrum and trispectrum. The bispectrum, which measures the correlation of phase between two different frequency components and quantifies the relationships among the underlying sinusoidal components of the EEG, has received considerable attention. The bispectrum specifically quantifies the relationship between sinusoids at two primary frequencies $f_1$ and $f_2$ and a modulation component at the frequency $f_1+f_2$. However, because the calculation must be performed using complex number arithmetic for several thousand $f_1$, $f_2$ and $f_1+f_2$ frequency combinations, the computations to obtain bispectral information are rather arduous. Another approach is to measure the "entropy" of the time domain EEG signal. This approach relies on an analysis of the complexity of the EEG signal to provide conclusions.

For clinical use, it is desirable to simplify the results of EEG signal analysis of the foregoing, and other types, into a workable parameter that can be used by an anesthesiologist in a clinical setting when attending the patient. Prior techniques have included showing the EEG signal in a relatively unprocessed form or showing a number (or letter) without any other underlying data supporting that number. Neither solution is helpful in a clinical setting; especially, in the case of the "number" indicator, when the number is at best a probability that the patient is not aware or conscious. Ideally, what is desired is a simple indicator that accurately indicates the patient's lack of awareness and how far below the transition to awareness the patient is. The indicator should also account for phenomena that varies by patient such as, for example, the less pronounced $\alpha$ peak of older patients and the possible occurrence of a burst suppression event. Thus, there remains a need for such an indicator that reliably and quickly indicates awareness during general anesthesia and the depth of anesthesia.

BRIEF SUMMARY OF THE INVENTION

Embodiments of the present invention relate to a system and method for determining from EEG signals the lack of awareness and the depth of anesthesia of a patient to whom an anesthetic agent is being administered. In particular, a log-log representation of the EEG power spectrum is converted to two intersecting lines so that the intersection point and the relative slopes can be analyzed to determine a state of anesthesia of a patient. This system and method may also be used in an analysis of the brain function of a sleeping individual to distinguish between awareness, REM sleep, and the various levels of non-REM sleep. It may also be used to investigate the effect of various experimental pharmaceuticals on brain function.

It is understood that other embodiments of the present invention will become readily apparent to those skilled in the art from the following detailed description, wherein it is shown and described only various embodiments of the invention by way of illustration. As will be realized, the invention is capable of other and different embodiments and its several details are capable of modification in various other respects, all without departing from the spirit and scope of the present invention. Accordingly, the drawings and detailed description are to be regarded as illustrative in nature and not as restrictive.

BRIEF DESCRIPTION OF DRAWINGS

Various aspects of a system and method for anesthesia monitoring are illustrated by way of example, and not by way of limitation, in the accompanying drawings, wherein.

DETAILED DESCRIPTION OF INVENTION

The detailed description set forth below in connection with the appended drawings is intended as a description of various embodiments of the invention and is not intended to represent the only embodiments in which the invention may be practiced. The detailed description includes specific details for the purpose of providing a thorough understanding of the invention. However, it will be apparent to those skilled in the art that the invention may be practiced without these specific details. In some instances, well known structures and components are shown in block diagram form in order to avoid obscuring the concepts of the invention.

Figure 1B:
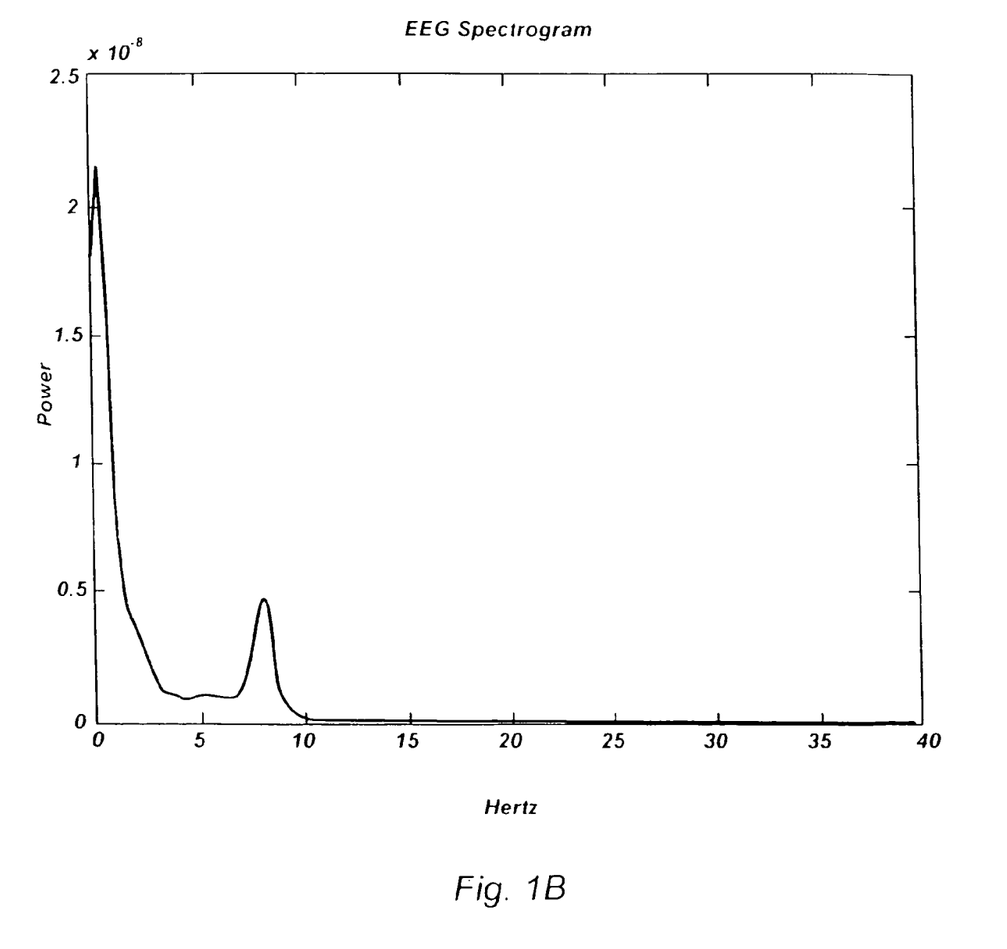
FIG. 1B shows an EEG spectrogram where the x-axis is linearly scaled and the y-axis is logarithmically scaled.
Figure 1C:
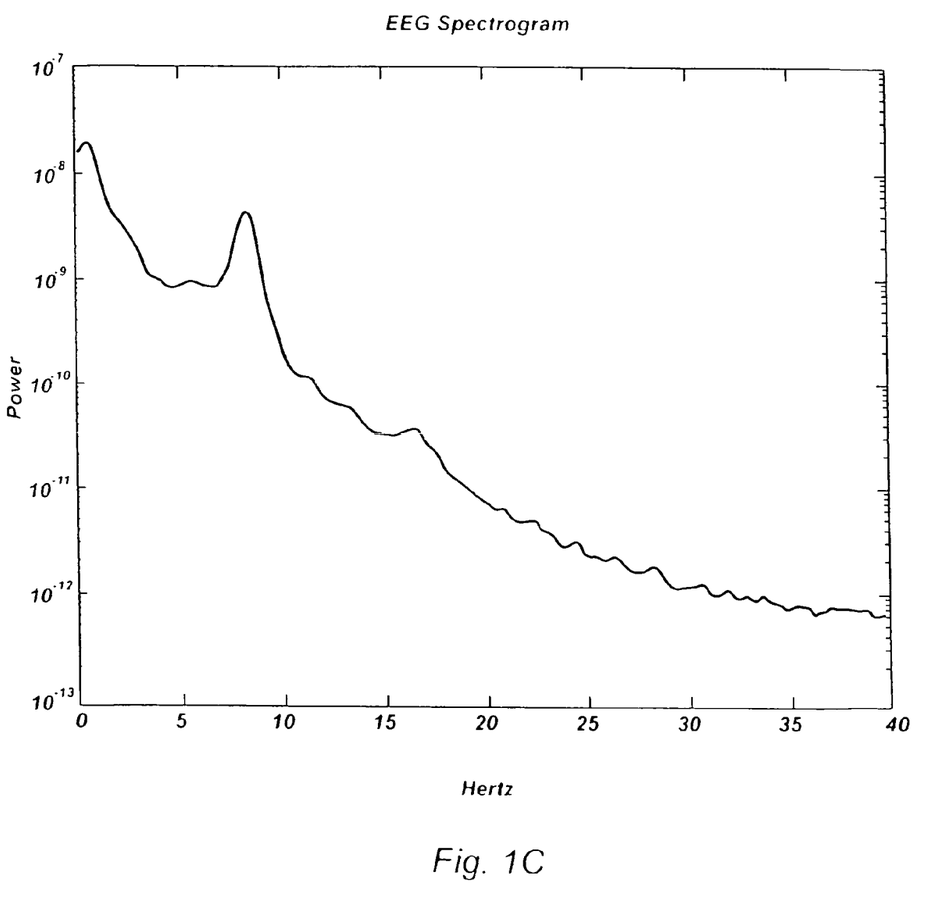
FIG. 1C shows an EEG spectrogram where both the x and y axes are linearly scaled.

FIGS. 1B and 1C illustrate common ways that EEG spectrograms can be displayed. In FIG. 1B the y-axis shows the power (scaled logarithmically) of the different frequencies present in the spectrogram. The x-axis is scaled linearly from about 0 to 40 Hz. In FIG. 1C, a similar spectrogram is shown but the y-axis is scaled linearly.

As discussed above a number of different techniques have been attempted to analyze these spectrograms in a way that would allow determination of the state of awareness and a level of anesthesia for a patient. However, finding an accurate and reliable indicator from analysis of these types of spectrograms has proven difficult. Prior apparatuses using numbers or letters have previously been used on large numbers of patients. There have been a significant number of cases reported where those indicators were inaccurate due to artifacts in the EEG signal. One advantage of the present system and method is that they can display the EEG spectrogram in a manner that is both an indicator of brain function and allows for the detection of artifacts or unusual situations at a glance. The present inventor has determined that a different view of the spectrogram data provides new insights to the amount and the usability of the information present in an EEG spectrogram that can be extracted to determine a lack of awareness and the state of anesthesia for a patient.

Figure 2:
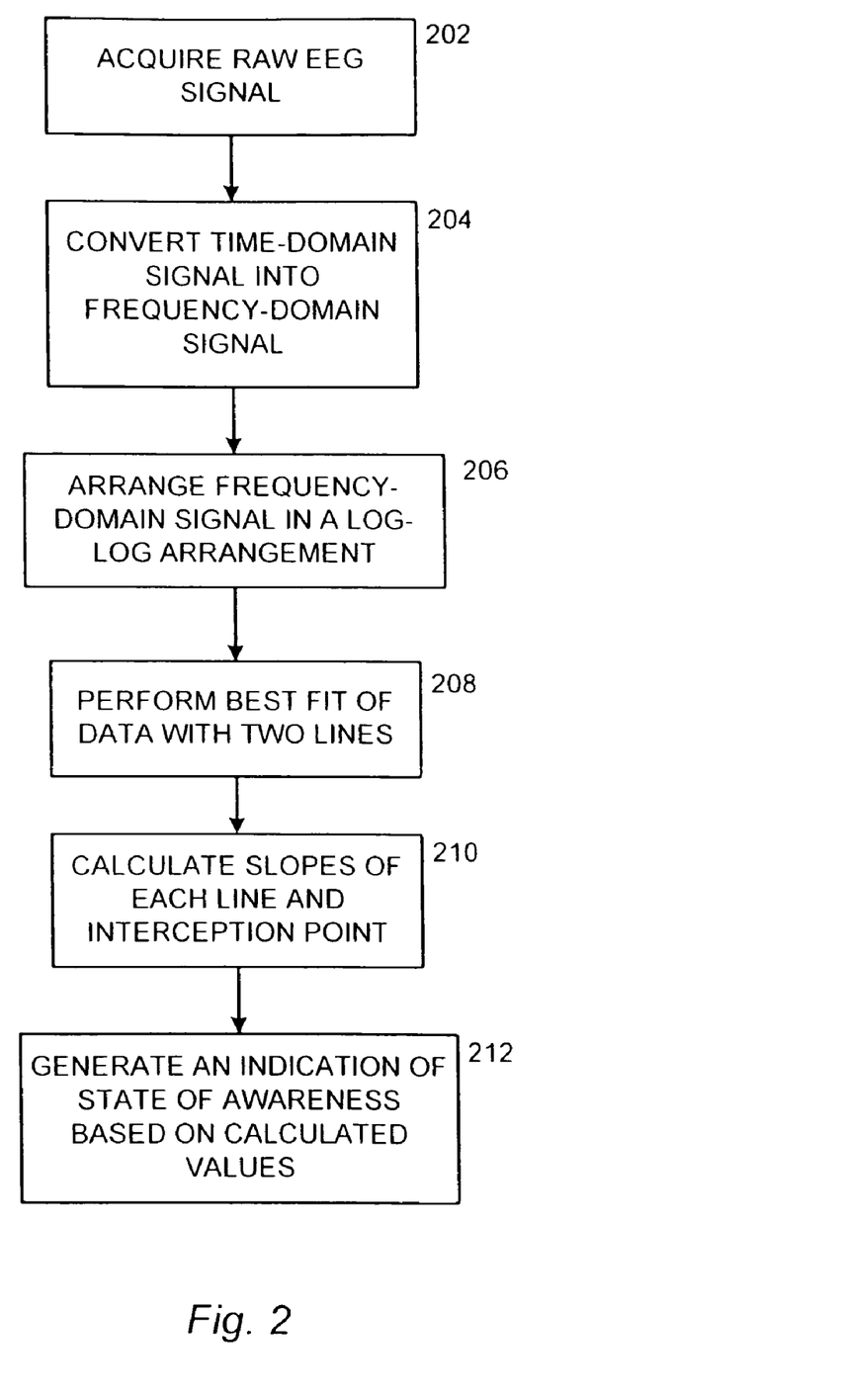
FIG. 2 shows a flowchart of an exemplary algorithm for analyzing EEG spectrograms in accordance with the principles of the present invention.

The flowchart of FIG. 2 depicts an exemplary algorithm for analyzing EEG spectrograms in accordance with the principles of the present invention. In step 202, the raw EEG signal is captured as is known in the art. Present techniques and devices as well as future-designed EEG devices may be utilized to acquire the raw signals. Also, as well known in the art, the raw signals may be filtered and processed to reduce noise and to remove artifacts that are known to be introduced into EEG signals. The raw signal is a time-domain series of samples that are sampled or converted to digital signals which can be then processed by computer platforms or specialized digital signal processors.

Once the digital signals are generated, the time-domain signal can be transformed into a frequency-domain signal in step 204. While there are a number of techniques for converting between the time domain and the frequency domain, a common technique involves the fast Fourier transform method. A number of computationally efficient algorithms for performing fast Fourier transforms beneficially result in a technique that can occur in almost real time with even limited computational power. As one of ordinary skill will recognize, there are a number of parameters that can be selected to control how the transform operates and performs. As an example, in one embodiment of the present invention, a two-second window averaged for periods of about one minute, or even longer, is used to convert the time-domain signal.

One novel realization reached by the present inventor is that the frequency domain signals are visually informative when arranged in a log-log format, in step 206. In particular, the y-axis represents the power, or power spectral density, of a frequency in the signal and the x-axis represent the frequency. Both axes, though, are scaled logarithmically. What results is a visual display that reveals that the resulting frequency-domain data can generally be split into two regions—the first region from about 0 to about 10 or 20 Hz and the second region representing the frequencies above the first (to about 40 Hz). The first range can extend further as well, especially when the patient is in a state of awareness These regions will be conveniently referred to a low frequency segment and a high frequency segment. Those labels are used as a way of convenience and of comparison to each other and are not intended to limit the segments in any way to a particular range of frequencies.

Once the frequency-domain data points are arranged in this log-log format, a best-fit line is calculated in steps 208. In particular, a first best fit line is calculated starting at the lower frequencies and moving higher while a second best fit line is calculated from the higher frequencies and moving lower. One of the easiest best-fit approaches is to use a least-squares approach but one of ordinary skill will recognize that there are numerous other data regression schemes that may be used to approximate a line while minimizing error. In one example, the best fit lines were accomplished using an iterative least-squares approach where the slope and y-intercept of a line providing the minimum mean square between the log of the spectral magnitude and that line were obtained. Also, one of ordinary skill will recognize that optional methods of fitting the data may be accomplished during the least-squares fit as well. For example, points that are statistical outliers can be discarded if their error size suggests that they should not be used when fitting the data to the best-fit line. The best-fit line can then be recalculated with the outliers ignored. By calculating a best-fit line from each direction two lines are calculated from the log-log power spectrogram. As mentioned, different regression methods other the least-squares may be used to calculate the best fit lines and furthermore, one regression method may be used for the high frequency line and a different regression method used for the low frequency line.

The determination of when the two lines are complete can be accomplished in a number of different ways. The determination can be based on an event in the EEG signal itself. For example, the EEG signal may exhibit an alpha-peak at a certain frequency and that value is used for the endpoints of the two best-fit lines. For example, the first best-fit line is calculated from the lowest frequency to the alpha-peak frequency and the second best-fit line is calculated from the alpha-peak frequency to the highest frequency. The alpha-peak frequency, itself, can be selected in different ways such as at the beginning of the peak, a center frequency, or at the end of the peak. Alternatively, the decision to stop the least-squares fitting can be determined on the fly as the best-fit lines are being calculated. For example, an analysis can be made to determine when a similar frequency is reached from both directions at which both the first best-fit line and the second best-fit line start deviating significantly (e.g., some percentage, such as, for example 3% to 8%) from the previously calculated best-fit line. This frequency, then, is the dividing point between the two best-fit line segments.

Once the two lines are determined, then the slope of each line can be calculated and the intersection point as well (see step 210). Of particular interest is the frequency at the intersection point. Based on the relative slopes of the two lines and the frequency of the intersection point, an indication is generated, in step 212, that relates to the state of anesthesia, or the state of awareness, of the patient.

Figure 3:
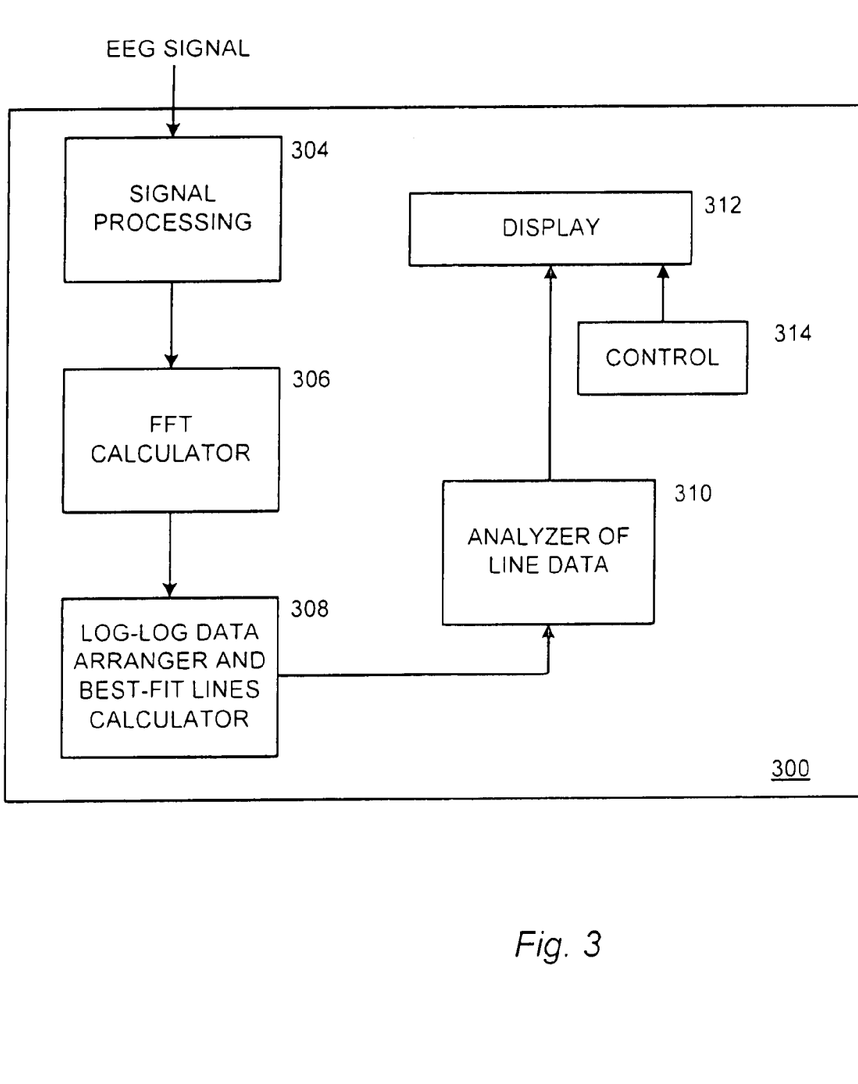
FIG. 3 shows an apparatus on which the flowchart of FIG. 2 may be performed in accordance with the principles of the present invention.

FIG. 3 illustrates an automated platform on which the algorithm described above may be implemented. In practice, the device 300 would be used during surgery to monitor the anesthesia state of the patient to allow an anesthesiologists to modify the delivery of an anesthetic agent as appropriate. The device 300 is shown in functional block form in FIG. 3 because the different functional blocks may be implemented in a variety of ways without departing from the scope of the present invention. For example, a programmable computer with a typical microprocessor may implement a variety of the functions in software programs that are stored on an accessible media and executed during operation. Alternatively, some of the functions may be implemented using specialized hardware including DSP chips and microcontrollers. One of ordinary skill will recognize that various combinations of hardware and software may be utilized to accomplish the functions of the blocks shown in FIG. 3.

The EEG signal 302 is received and then filtered and converted by a signal processor 304. That signal can then be transformed into the frequency domain by a fast Fourier transformer 306. The power spectrum of the frequency domain signal can then be calculated in a log-log arrangement so that an interpolator 308 can calculate two best-fit lines for the spectrum. An analyzer 310 analyzes the two best fit lines to determine their respective slopes and the frequency at which they intersect.

Based on the calculations of the analyzer 310 a display 312 provides an indication of the anesthesia state of the patient. The display 312 may be multifaceted to provide the viewer of the display with different information. Two particularly relevant pieces of data are a) the difference between the slopes of the two best-fit lines and b) the frequency at which the two lines intersect. Thus, these two values may be displayed as raw numeric information. A graphical display may be included which graphs these values in a historical fashion so that the viewer of the display can see how the values have been changing in some preset time period. For example, the display could show the values over a window depicting the last 5 minutes. A control 314 for the display 312 can be used to allow the viewer to change between different formats of output as desired. The display 312 can also be configured to display the best-fit lines in near real-time with (or without) the two values discussed above. Also, (not shown) the device 300 may included a storage function that records various signals and calculations during the duration of the surgery.

Figure 4:
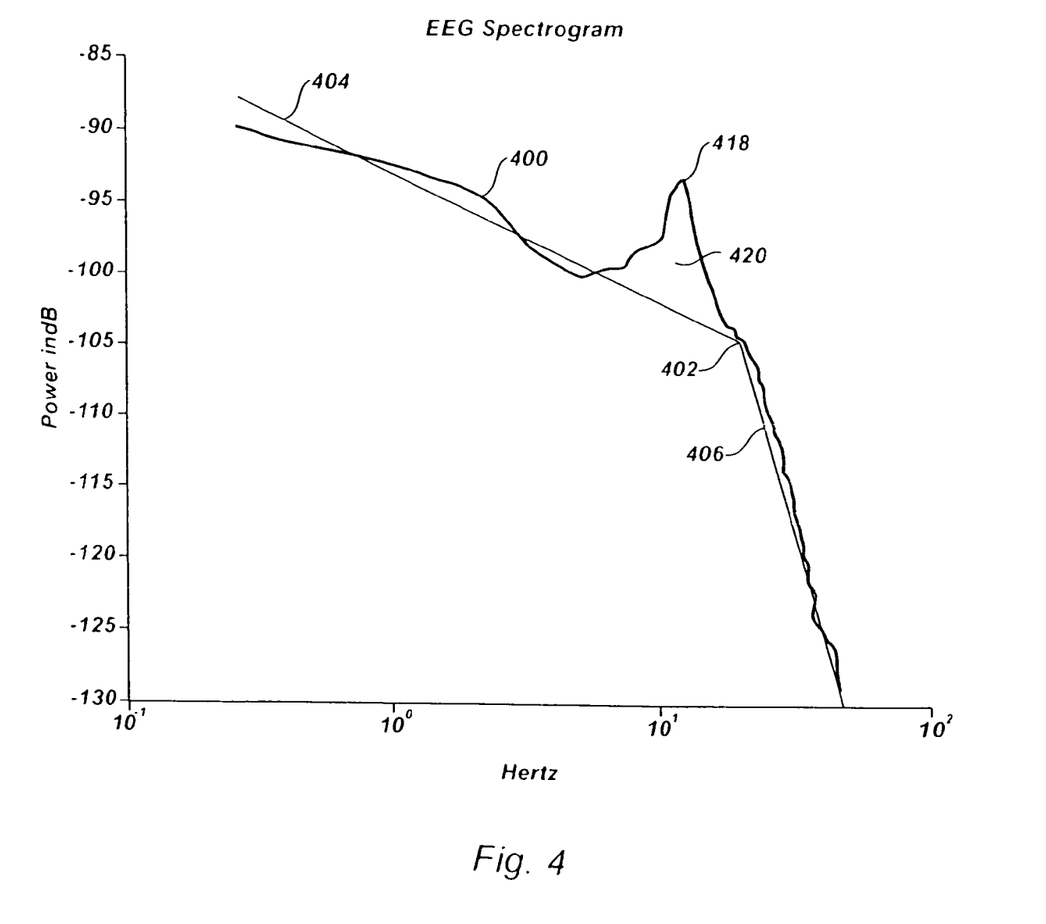
FIG. 4 shows an exemplary presentation format of an EEG spectrogram in accordance with the principles of the present invention.

FIG. 4 shows an exemplary log-log EEG power spectrogram in accordance with the principles of the present invention. The spectrogram 400 is that of a patient that is deeply under anesthesia. In other words, the patient has crossed the transition point into a lack of awareness and is relatively far from returning to that transition point. As shown, the power of frequencies above about 12 or 15 Hz significantly drops while the power at the lower frequencies is much higher. By applying the algorithm discussed in relation to FIG. 2, the spectrogram 400 can be transformed into the best-fit lines 404, 406. Regardless of the point of reference from which you measure, the respective slopes of the low frequency line 404 and the high frequency line 406 are vastly different. The intersection point 402 is at about 15 Hz.

Figure 5:
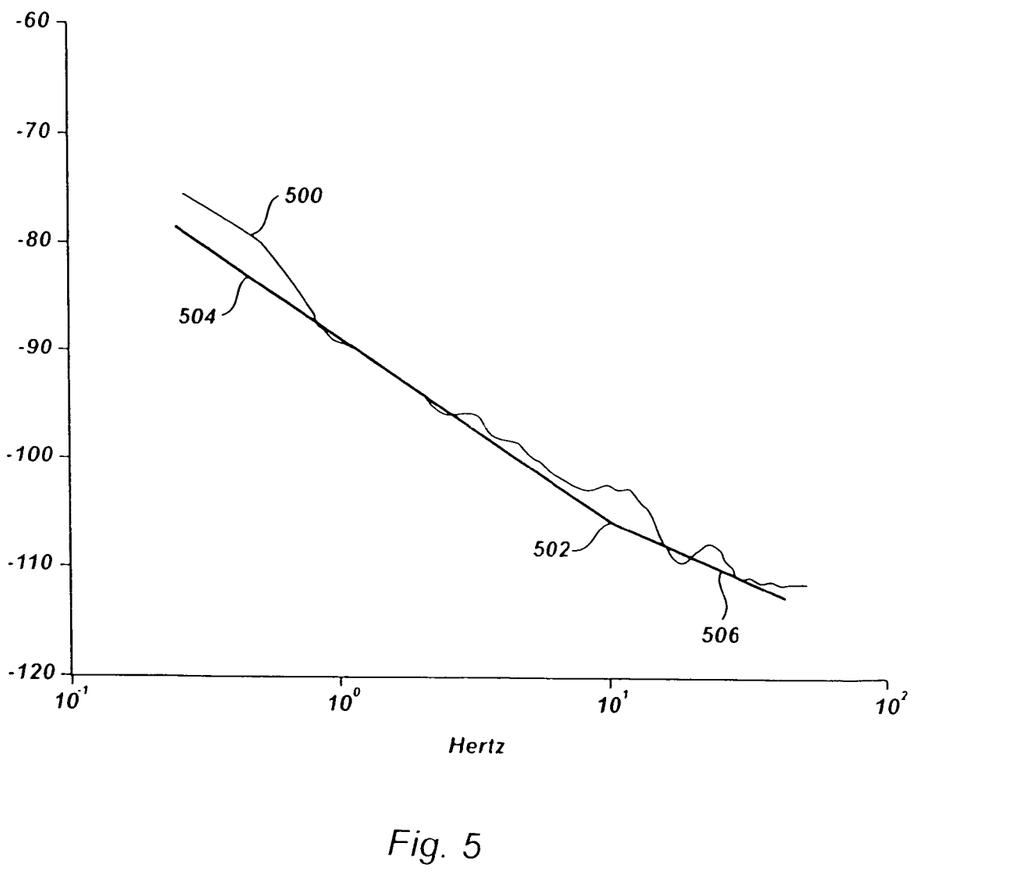
FIG. 5 shows the exemplary presentation format of FIG. 4 with another EEG spectrogram in accordance with the principles of the present invention.

FIG. 5 shows an exemplary log-log EEG spectrogram in accordance with the principles of the present invention as well. The spectrogram 500 is that of a patient that is awake or almost so. One visually noticeable difference from FIG. 4 is that the slopes of the two line segments 504, 506 are similar in magnitude. The intersection point 502 is at about 10 Hz.

A series of snapshots of the log-log EEG power spectrogram would show the transition from FIG. 4 to FIG. 5 of the waking of a patient that is deeply anesthetized. The high frequency line would be depicted with a slope that gradually becomes more level and approaches that of the low-frequency line. The intersection point of the two lines would travel back and forth around the 10 to 15 Hz point and maybe even higher to about 20 Hz. This visual data included in such graphs as they change over time, as well as quantifiers that can be extracted from them, allow for a real time determination of the anesthesia state of the patient.

While a skilled anesthesiologist will rely on a variety of observations and professional judgments to monitor a patient state under anesthesia, the following general rules have been discovered based on the embodiments of the present invention discussed above. For a point of reference, the high frequency line 406 is "steep" as compared to the high frequency line 506 and is typical of a deeply anesthetized patient. When the slope of the high frequency line becomes more "shallow" and approaches to about 20 degrees or less of the slope of the low frequency line, it indicates that the patient is moving from a deeper state of anesthesia to a shallower state and may be aware of sensation. When the slope of the high frequency line surpasses that of the low frequency line, then the patient is generally awake. Also, generally, the more power seen in the higher frequencies the more awake a patient is.

For ease of use, a binary indicator (e.g., a red/green light) can be used to indicate whether or not a patient is in a deep enough state of anesthesia to perform surgery. However, a three-level indicator (e.g., red/yellow/green) provides additional benefits. The "green" level would indicate that the patient is very likely unconscious. The "red" level would indicate that the patient is very likely awake. The "yellow" level represents an uncertainty region where an anesthesiologist would likely more closely monitor the state of the patient because there is less certainty as to what awareness state the patient is in and so there is a risk of the possibility that the patient is aware.

When the intersection of the two lines is about 20 Hz and the relative slopes are about equal (e.g., within about 5 degrees or less), then there is a very high probability that the patient is awake. Especially when the slope of the best-fit high-frequency line is shallower than the best-fit low-frequency line, the patient is considered to be awake. Thus, the display 312 would be "red" at this time. As the patient continues to be monitored, the display 312 could transition to "yellow" when the slope of the high frequency line changes so as to become more steep than the low frequency line.

While the exact parameters can be set based on factors such as the medical history of the patient, the age of the patient, and a reference EEG power spectrum, in general terms if the intersection points of the two lines are between about 12 and 18 Hz, or below, and the slope of the high frequency line is about 20 or more degrees steeper than the low frequency line, then the display 312 could transition to green showing that there is a high probability that the patient is now considered to be under anesthesia or, in other words, be unaware of sensation. During surgery, the display can continue to be monitored to allow the anesthesiologist to deliver the anesthetic agent in a controlled fashion. Accordingly, warnings or blinking lights could be used to indicate when the slope of the lines are becoming too similar or the intersection point is moving outside the safe range and back to the uncertain or "yellow" range. In one embodiment, the "display" could be aural rather than visual so that by sound cues the anesthesiologist can be informed of what is transpiring without requiring him to look at a display.

Figure 6:
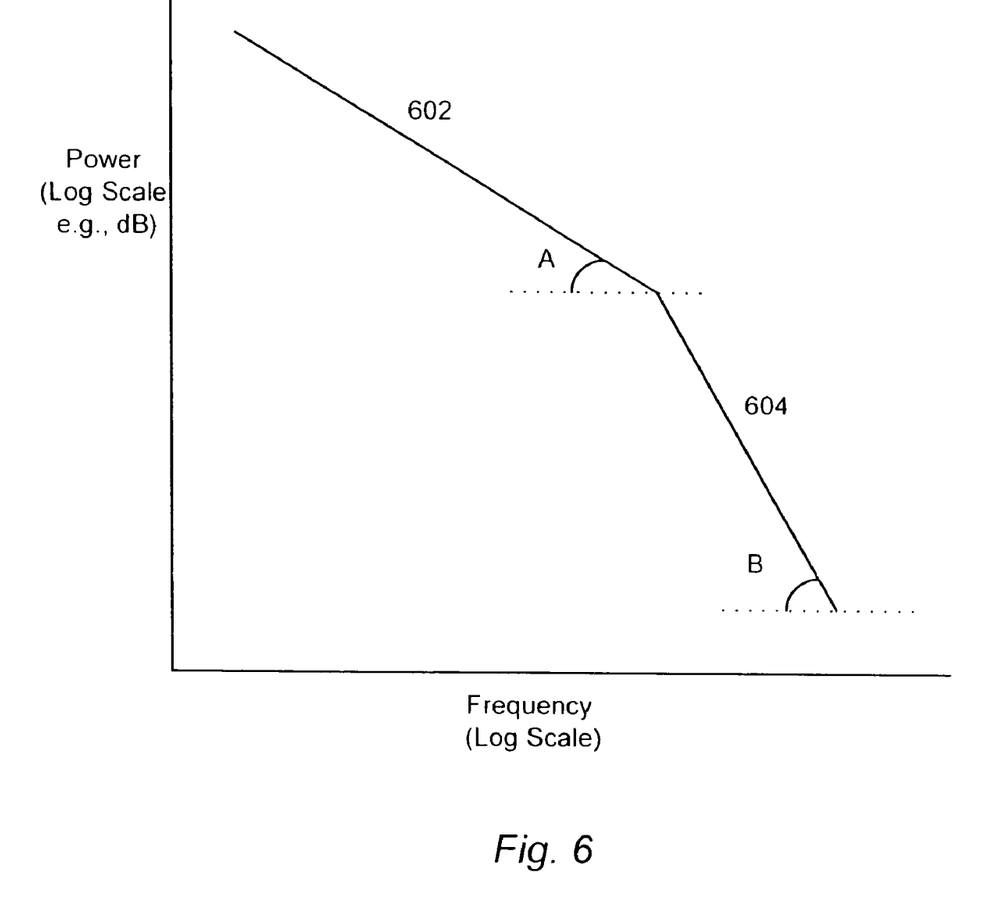
FIG. 6 shows another example of the graph similar to that of FIGS. 4 and 5.

As a way to further explain the features of the display of FIGS. 4 and 5, FIG. 6 is provided showing angles A and B. Depending on where a reference point is chosen and how the slopes of lines 602 and 604 are measured, the values may be negative or positive and, therefore, discussing "greater than" and "less than" may be ambiguous. Accordingly, what is meant in the above discussion is that angle A represents the slope of the low frequency line 602 and angle B represents the slope of the high frequency line 604. In FIG. 6 the magnitude of angle B is larger than that of angle A. Thus the high frequency line 604 is steeper than the low frequency line 602. As the slope of line 604 changes and becomes more shallow, the angle B becomes closer to equaling angle A. When the difference between angle A and angle B approaches about 20 degrees and greater, then a patient is considered to be in a state of unawareness.

For example, the angle B can be changing so as to become smaller (i.e., the line 604 becomes more shallow), then as the difference between angle A and angle B approaches about 20 degrees the patient is considered to be transitioning from unconsciousness to a state where it is uncertain whether or not they are unconscious. For example, because in one embodiment the data forming the best-fit lines is averaged over the last minute, the patient may have been aware for the last 5 seconds but unaware for the previous 55 seconds. Thus, there is some uncertainty about whether the patient is aware or unconscious. When fully aware, a patient's graph may have a high frequency line 604 that moves such that the angle B is equal to or less than the angle A (as in FIG. 5). The frequency of the intersection point of the two lines is helpful when the state of the patient is uncertain. For example, the higher that frequency, the more likely the patient is aware. Thus, an anesthesiologist can monitor the display 312 during this uncertainty period to administer an anesthetic agent in an appropriate manner.

In reverse, a shallow line 604 can move so as to become steeper (thus increasing the angle B) as a result of a patient entering natural sleep or being given an anesthetic agent.

When the difference between angles A and B grows and approaches to about 20 degrees the patient is considered to be transitioning into a state of unawareness. As the patient moves further from this transition point, the angle B becomes significantly steeper than angle A (such as FIG. 4) and the patient is considered to be unaware. Thus, the EEG spectrogram itself is used as an indicator as to whether a patient is in a state of awareness or a state of unawareness.

In the discussion above, a difference in the two angles of about 20 degrees is used as an example of where the transition between "lack of awareness" and "uncertainty" occurs and when the two angles are about equal is used as an example of where the transition between "awake" and "uncertainty" occurs. However, one of ordinary skill will recognize that embodiments the present invention are not intended to be limited to these specific values. Because the physiology of people (or non-human patients even) can differ while still remaining within the acceptable norm, the transition point for one patient will not always align exactly with the transition point for another patient. Thus, there will be a value where there is an extremely high certainty that every patient is aware and another value where there is similar confidence that every patient lacks awareness. And, as stated above, between these two values, is an uncertain region in which some patients may be aware while others are not. Therefore, embodiments of the present invention contemplate selecting parameters that affect the size of this uncertainty region. For example, the consequences of being incorrect differ significantly if the monitoring is part of a sleep architecture study as compared to a patient undergoing surgery. In the first instance, an inconsequential miscalculation of a patient's restful sleep periods may result; but in the second instance a potentially far-reaching traumatic event may occur with the patient being aware during surgery. In the second case, the parameters of the system may be selected to err on the side of safety as compared with the first case.

Furthermore, the difference value between the two angles at which it is determined that a transition is occurring can use different ranges of values. For example, when determining if a patient is leaving the state where it is certain they are unaware, the value of the angle difference where transition is considered to occur can be selected from a range of between about 30 to 15 degrees for the two lines. The larger the difference value is, the less likely that a patient will wake up without it being detected. Conversely, when determining if a patient is transitioning from "uncertain" to a high probability of being unaware, the value of the angle difference where transition is considered to occur can be selected from a range of between about 20 to 35 degrees for the two lines. The higher this value is, the less likely is will be to falsely determine a patient is unconscious when they are actually aware.

Although, the general discussion provided above has focused on anesthesia and patient awareness during surgery, embodiments of the present invention are useful in other situations as well. For example, analyzing sleep behavior of a patients may be accomplished as well. It is useful to be able to distinguish between a REM sleep state, different levels of non-REM sleep, and an awake state of an individual.

Figure 7A:
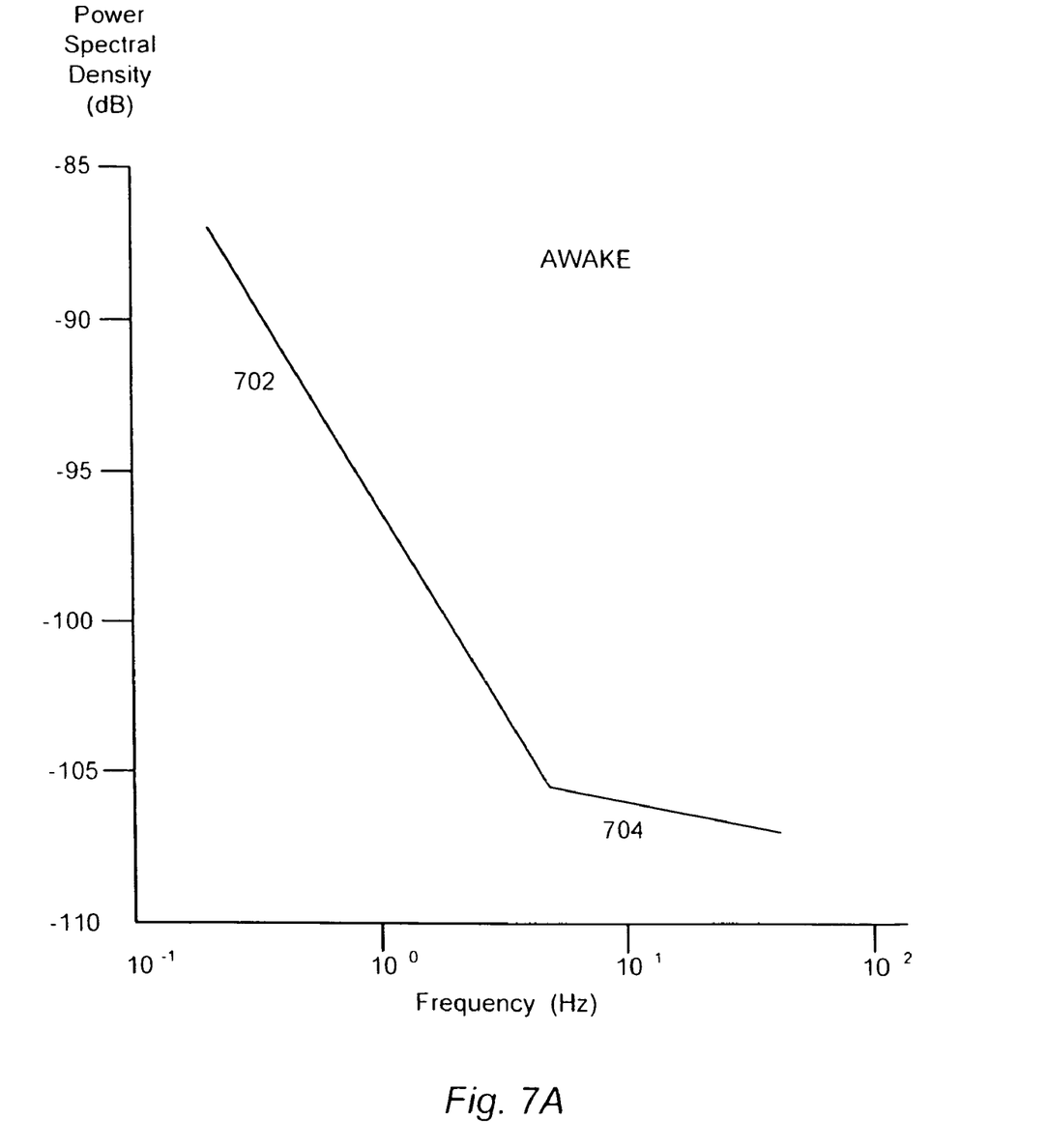
FIGS. 7A-7D show a series of EEG spectrograms in accordance with the principles of the present invention that indicate brain function of a sleeping individual.
Figure 7B:
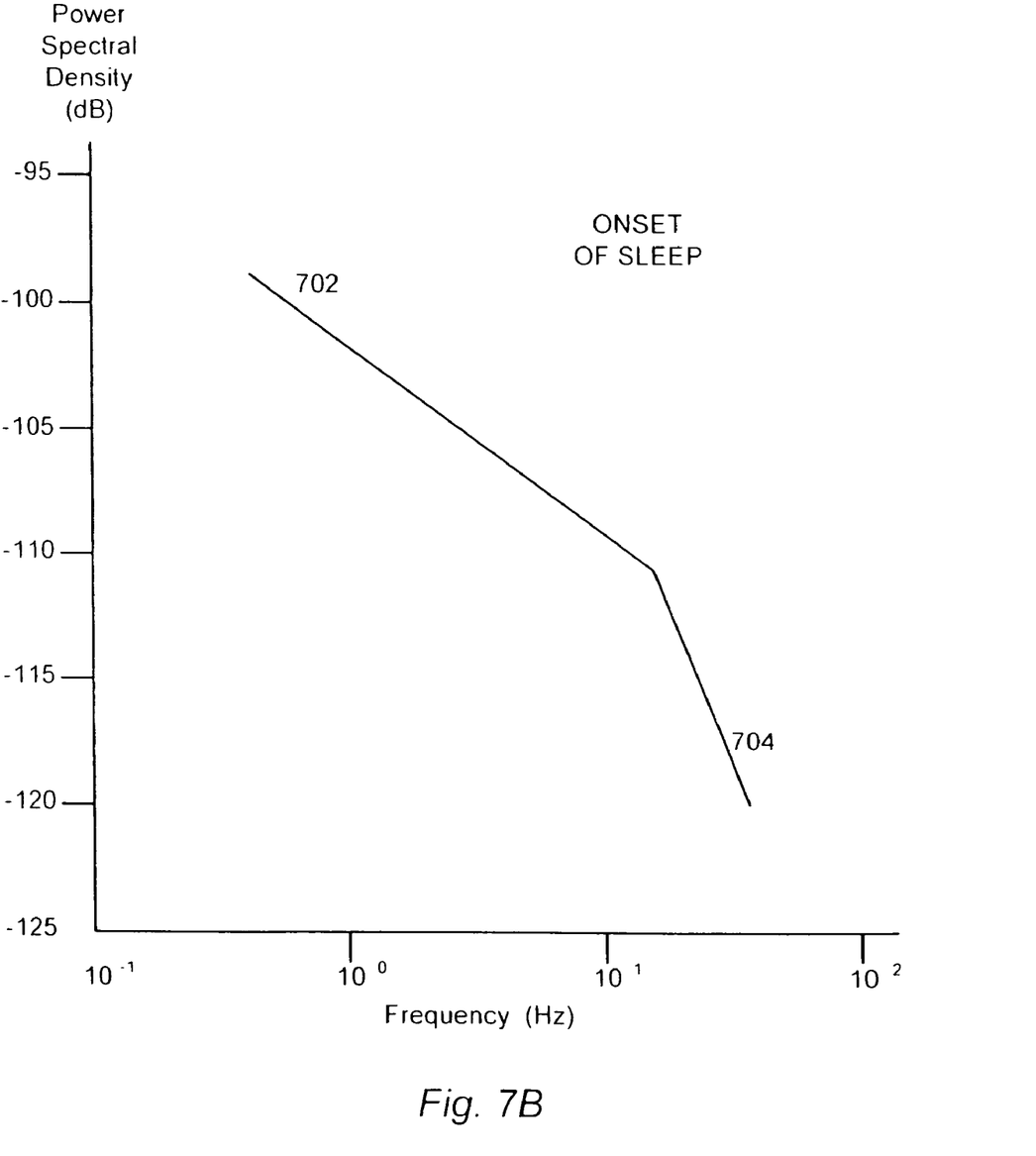
Figure 7C:
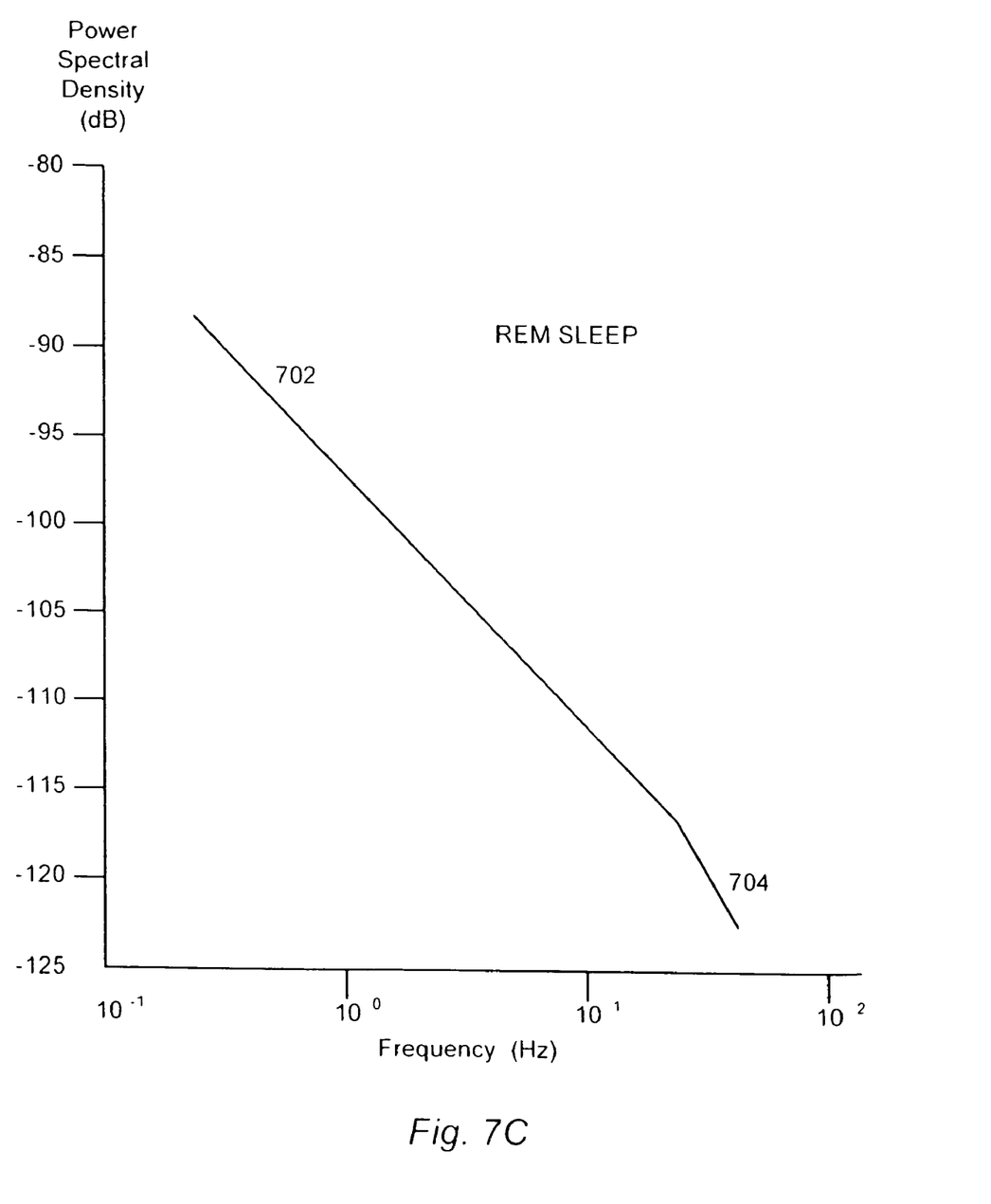
Figure 7D:
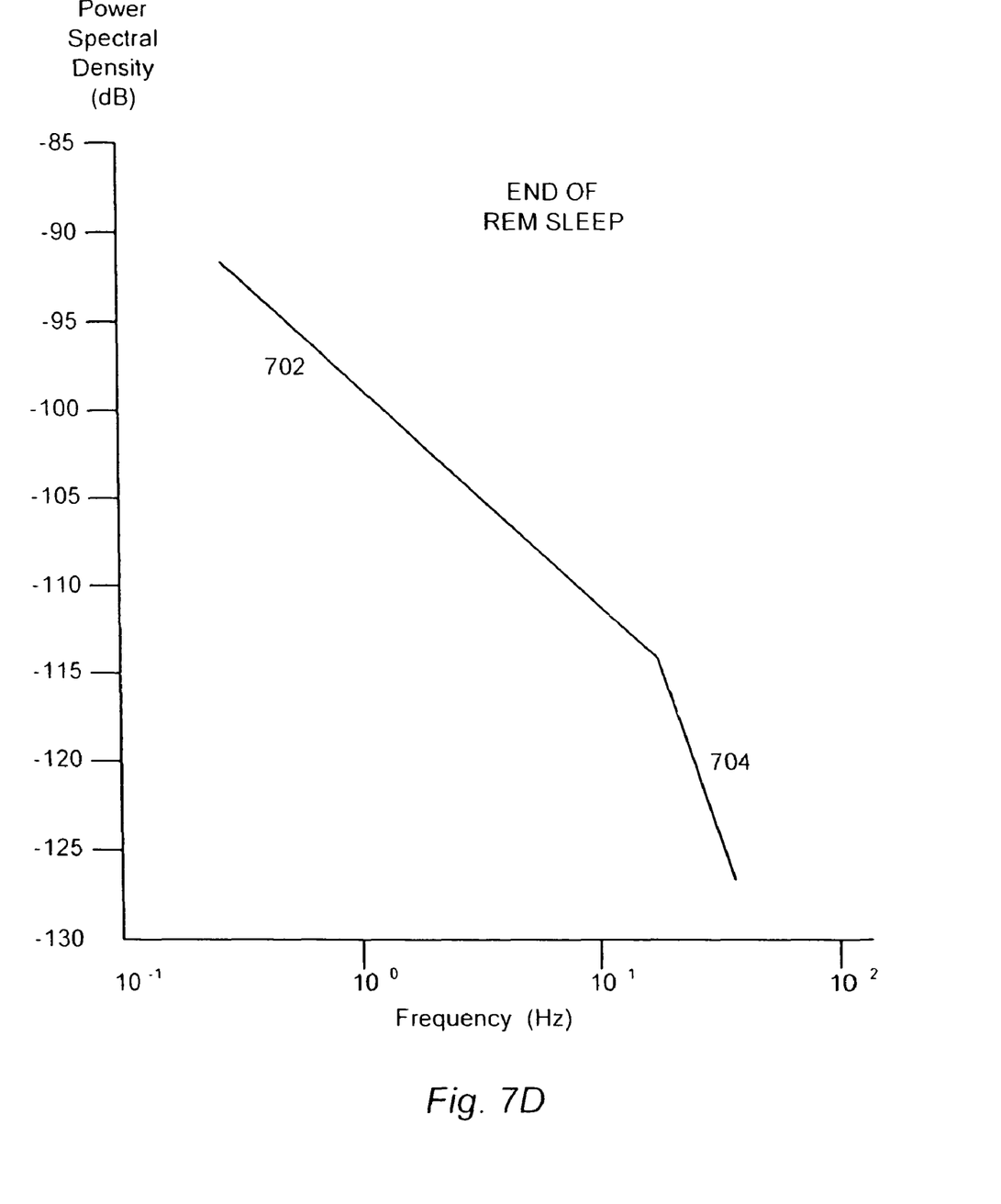

The series of FIGS. 7A-7D show embodiments of the present invention utilized to display brain functions of a person during different periods of sleep. Similar to FIGS. 4-6, each of these graphs includes a low frequency best fit line 702 and a high frequency best fit line 704 which intersect at an intersection point. FIG. 7A is that of an awake (or aware) person. The high frequency line 704 is shallower than the low frequency line 702. However, as the person begins to enter an asleep state, the line 704 moves so as to be steeper than the low frequency line 702. as shown in FIG. 7B. During sleep, a person will enter REM sleep which is useful for monitoring for various reasons. The display of a person in REM sleep (see FIG. 7C) resembles that of an awake person. Thus, if other bio sensors indicate the person is asleep, then the different displays of FIGS. 7B and 7C can be used to determine if the person is in REM sleep or a lighter stage of sleep (non-REM sleep). As a person leaves REM sleep to return to non-REM sleep, the display returns to that of FIG. 7D. Within, non-REM sleep, there are different levels of sleep which can be observed by watching the change in angles of the two lines from one indicating deep sleep (e.g., a large difference in the angles of the two lines) and ones indicating lighter sleep (e.g., progressively smaller differences in the two angles). Thus, similar to the techniques discussed above, the state of awareness of a person can be determined by the present, novel method of utilizing an EEG spectrogram as the indicator. In this second example, the state of awareness relates to natural sleep states not the unconsciousness resulting from administering an anesthetic agent.

Additional useful data can be extracted from the graph depicted in FIG. 4. In this graph, an alpha peak 418 is present that would typically be considered an outlier when calculating the best fit line 404. Other peaks may occur in the EEG signal 400 and may be useful as well. One beneficial analysis of such peaks is to use the best fit line 404 as a baseline and subtract it from the signal 400. For the alpha peak 418, for example, the area 420 above the baseline represents information about the alpha peak. For example, its amplitude, its spread, and the center frequency can all be determined by analyzing the area 420. Regression analysis of these parameters revealed that there is a correlation between the alpha peak frequency and concentration of the anesthetic agent. Thus, because the alpha peak generally shifts with concentration of anesthesia (decreasing frequency as concentration increases), the changes in the alpha peak can be used as additional information or confirmation when making a determination about the state of awareness of the patient. In some tests, surgical stimulation (e.g., retracting an inflamed nerve root) also resulted in changes of the alpha peak size and location such as reducing the amplitude of the alpha peak and or shifting it to a higher or lower frequency. These additional factors may be useful when determining the state of awareness of the patient.

One of ordinary skill will recognize that performing many of the steps of the various embodiments of the present invention occur automatically within an appropriately configured programmable computer which can implement the steps described in FIG. 2. These steps may occur logically or physically. For example, one display described above explicitly provides a visual representation of the best-fit lines. However, the principles of the present invention may alternatively be accomplished without actually drawing such lines. The slopes and intercepts of the lines may be calculated (without drawing, or displaying, them) so that their intersection point and relative angles may be calculated and used for indicating an awareness state of a patient. Similarly, arranging the power spectrum in a log-log arrangement does not necessarily require a physical display of such data but, rather, relates to the analysis or treatment of the data such that an iterative step in the x-direction is a logarithmic sized step in frequency and an iterative step in the y-direction is a logarithmic sized step in power, or power density. For that matter, the principles of the present invention may also be practiced if the axes are flipped as well. Additionally, the "slopes" of each best-fit line represents the rate in change of power over the rate in change of frequency (in a log-log arrangement); thus calculating the difference in degrees of the slopes may similarly be accomplished by a comparison of the magnitudes of the different slopes without physically converting each slope into a specific angular value.

The previous description is provided to enable any person skilled in the art to practice the various embodiments described herein. Various modifications to these embodiments will be readily apparent to those skilled in the art, and the generic principles defined herein may be applied to other embodiments. For example, the terms "patient" and "individual" have been used herein generally to refer to a human being. However, many mammals have brains that exhibit similar brain functions as described herein and, thus, embodiments of the present invention are contemplated which involve non-human patients as well such as, for example, but not limited to dogs, primates, rats, etc. Thus, the claims are not intended to be limited to the embodiments shown herein, but are to be accorded the full scope consistent with each claim's language, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A method for providing an indication of a state of awareness for a patient, comprising the steps of:
arranging data of an EEG power spectrogram to provide power versus frequency in a log-log arrangement;
calculating a first best-fit line for a lower frequency region of the EEG power spectrogram, using a processor having access to the data;
calculating a second best-fit line for a higher frequency region of the EEG power spectrogram, using the processor; and
displaying, on a display device, an indication of the state of awareness based on the first and second best-fit lines.

2. The method of claim 1, further comprising the steps of:
acquiring an analog time-domain EEG signal; and
converting the analog time-domain EEG signal into a digital time-domain EEG signal.

3. The method of claim 2, further comprising the steps of:
transforming the digital time-domain EEG signal to a frequency-domain EEG signal; and
calculating the EEG power spectrogram based on the frequency-domain EEG signal.

4. The method of claim 1, wherein:
calculating the first best-fit line further includes the step of performing a least-squares fit of power values for frequencies between a lowest frequency and an intersection frequency; and
calculating the second best-fit line further includes the step of performing a least-squares fit of power values for frequencies between a highest frequency and the intersection frequency.

5. The method of claim 1, wherein the first and second best-fit lines intersect at an intersection frequency.

6. The method of claim 5, further comprising:
calculating a first slope of the first best-fit line and a second slope of the second best-fit line.

7. The method of claim 6, wherein the indication is determined based, at least in part, on a difference between the first and second slopes.

8. The method of claim 7, wherein the indication is determined, at least in part, on the intersection frequency.

9. The method of claim 8, wherein if the first and second slopes are greater than about 20 degrees in difference, then the indication indicates the patient is in a state lacking awareness.

10. The method of claim 8, wherein if the first and second slopes are substantially the same, then the indication indicates the patient is in an awake state.

11. The method of claim 1, further comprising:
monitoring a first slope of the first best-fit line and a second slope of the second best-fit line;
determining a transition occurs where a difference between the first and second slopes changes from being greater than about 20 degrees to less than about 20 degrees; and
based on the transition occurring, indicating on the display device that there is a risk the patient is aware.

12. The method of claim 1, wherein the step of displaying further includes the steps of:
displaying the first and second best-fit lines in a near real time manner.

13. The method of claim 1, wherein the step of displaying further includes the steps of:
displaying an intersection frequency of where the first and second best-fit lines intersect; and
displaying a difference between a first slope of the first best-fit line and a second slope of the second best-fit line.

14. The method of claim 1, wherein the step of displaying further includes:
receiving input to control the display device to select from among different display formats.

15. The method of claim 1, wherein the indication indicates one of REM sleep, non-REM sleep, and awakeness.

16. An apparatus for providing an indication of a state of awareness for a patient, comprising:
a data formatter configured to arrange data of an EEG power spectrogram, that provides power versus frequency, in a log-log arrangement;
a first calculator configured to calculate a first best-fit line for a lower frequency region of the EEG power spectrogram;
the first calculator also configured to calculate a second best-fit line for a higher frequency region of the EEG power spectrogram; and
a display configured to provide an indication of the state of awareness based on the first and second best-fit lines.

17. The apparatus of claim 16, further comprising:
a receiver configured to acquire an analog time-domain EEG signal;
a converter configured to convert the analog time-domain EEG signal into a digital time-domain EEG signal;
a transformer configured to transform the digital time-domain EEG signal to a frequency-domain EEG signal; and
a second calculator configured to calculate the EEG power spectrogram based on the frequency-domain EEG signal.

18. The apparatus of claim 16, wherein the first calculator is configured to calculate the first best-fit line by performing a least-squares fit of power values for frequencies between a lowest frequency and an intersection frequency; and wherein the first calculator is also configured to calculate the second best-fit line by performing a least-squares fit of power values for frequencies between a highest frequency and an intersection frequency.

19. The apparatus of claim 18, further comprising:
an analyzer configured to calculate an intersection frequency of the first and second best-fit lines, a first slope of the first best-fit line, and a second slope of the second best-fit line.

20. The apparatus of claim 19, wherein the indication is based, at least in part, on a difference between the first and second slopes and the intersection frequency.

21. The apparatus of claim 16, wherein the indication indicates one of REM sleep, non-REM sleep, and awakeness.

* * * * *